US010011815B2

(12) United States Patent
Schetters et al.

(10) Patent No.: US 10,011,815 B2
(45) Date of Patent: Jul. 3, 2018

(54) METHOD TO SPORULATE COCCIDIAL OOCYSTS PURIFIED FROM ANIMAL FAECES, SPORULATED OOCYSTS OBTAINED WITH THIS METHOD AND A VACCINE CONTAINING THESE SPORULATED OOCYSTS

(71) Applicant: Intervet Inc., Madison, NJ (US)

(72) Inventors: Theodorus Petrus Maria Schetters, Cuijk (NL); Koen Gevers, Boxmeer (NL)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 15/300,522

(22) PCT Filed: Apr. 2, 2015

(86) PCT No.: PCT/EP2015/057298
§ 371 (c)(1),
(2) Date: Sep. 29, 2016

(87) PCT Pub. No.: WO2015/150513
PCT Pub. Date: Oct. 8, 2015

(65) Prior Publication Data
US 2017/0114320 A1    Apr. 27, 2017

(30) Foreign Application Priority Data
Apr. 3, 2014   (EP) .................... 14163330

(51) Int. Cl.
| *A61K 39/00* | (2006.01) |
| *A61K 39/002* | (2006.01) |
| *A61K 45/00* | (2006.01) |
| *C12N 3/00* | (2006.01) |
| *A61K 39/012* | (2006.01) |
| *C12M 1/26* | (2006.01) |
| *C12M 3/04* | (2006.01) |

(52) U.S. Cl.
CPC .............. *C12N 3/00* (2013.01); *A61K 39/012* (2013.01); *C12M 27/10* (2013.01); *C12M 33/14* (2013.01)

(58) Field of Classification Search
CPC .............. A61K 39/00; A61K 39/012
USPC ................. 424/184.1, 265.1, 278.1
See application file for complete search history.

(56) References Cited

U.S. PATENT DOCUMENTS 5,068,104 A * 11/1991 Bhogal ................ A61K 39/012
424/193.1

FOREIGN PATENT DOCUMENTS

| WO | 200237961 A2 | 5/2002 |
| WO | 2003020917 A1 | 3/2003 |

OTHER PUBLICATIONS

Graat, E.A.M., et al. Parasitology, vol. 108, pp. 497-502, 1994.*
Al-Badri, R., et al., Parasitology Research, vol. 111, pp. 1947-1952, 2012.*
Duszynski Donald W. et al, External factors and self-regulating mechanisms which may influence the sporulation of oocysts of the rat coccidium eimeria nieschulzi, International Journal of Parasitology, Feb. 1977, pp. 83-88, vol. 7, No. 1.
Extended European Search Report for 14163330.5 dated Oct. 20, 2014.
Graat, E A M et al, Rate and course of sporulation of oocysts of Eimeria acervulina under different environmental conditions, Parasitology, Jun. 1994, pp. 497-502, vol. 108, No. 5.
International Search Report forPCT/EP20151057298 dated Jun. 26, 2015, 4 sheets.
Riadh Al-Badri et al, The kinetics of oocyst shedding and sporulation in two immunologically distinct strains of Eimeria maxima, GS and M6, Parasitology Research, Jul. 25, 2012, pp. 1947-1952, vol. 111, No. 5.
Waldenstedt, L et al, Sporulation of Eimeria maxima Oocysts in Litter with Different Moisture Contents, Poultry Science, Oct. 2001, pp. 1412-1415, vol. 80, No. 10.

* cited by examiner

Primary Examiner — Rodney P Swartz

(57) ABSTRACT

The invention pertains to a method to sporulate coccidial oocysts purified from animal faeces (5), the method comprising providing the purified oocysts as a layer (40) on a supporting surface (22), maintaining the layer at least intermittently in an oxygen containing gaseous environment (60) having a relative humidity of at least 15% and maintaining the temperature of the oocysts between 19° C. and 37° C. The invention also pertains to sporulated oocysts obtained with this method and to a vaccine containing such sporulated oocysts.

12 Claims, 4 Drawing Sheets

Figure 1:
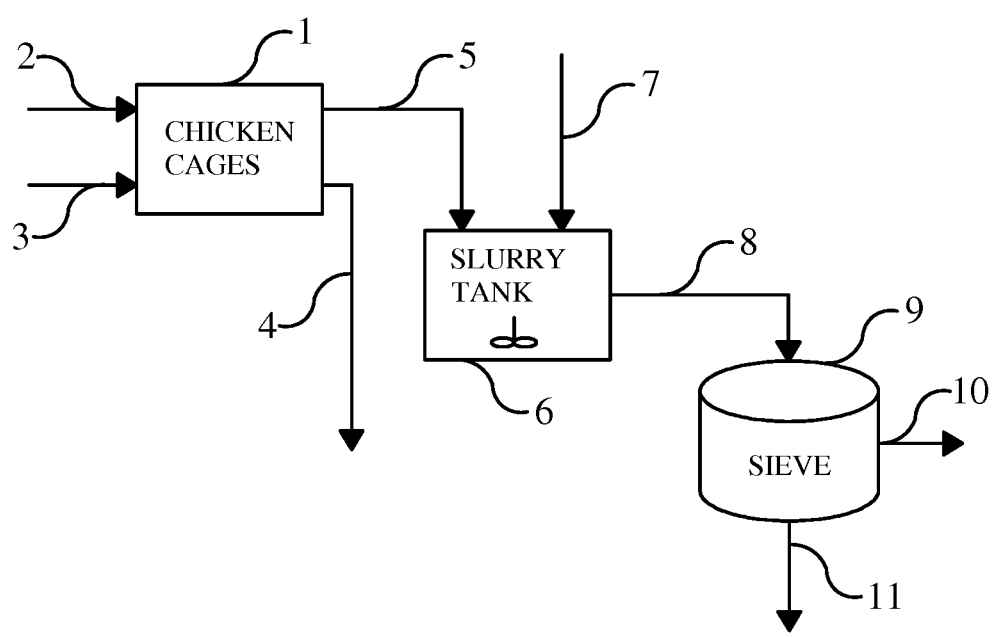

METHOD TO SPORULATE COCCIDIAL OOCYSTS PURIFIED FROM ANIMAL FAECES, SPORULATED OOCYSTS OBTAINED WITH THIS METHOD AND A VACCINE CONTAINING THESE SPORULATED OOCYSTS

CROSS-REFERENCE TO RELATED APPLICATIONS

This application is a national stage entry under 35 U.S.C. § 371 of PCT/EP2015/057298 filed on Apr. 2, 2015, which claims priority to EP Application No. EP14163330.5 filed on Apr. 3, 2014. The content of PCT/EP2015/057298 is hereby incorporated by reference in its entirety.

GENERAL FIELD OF THE INVENTION

The invention pertains to a method to sporulate coccidial oocysts purified from animal faeces. The invention also pertains to sporulated oocysts obtained with this method and to a vaccine containing such sporulated oocysts.

BACKGROUND OF THE INVENTION

Coccidiosis is a disease of various animals in which the intestinal mucosa is invaded and damaged by a protozoa of the subclass Coccidia. The economic effects of coccidiosis can be especially severe in the poultry industry where intensive housing of birds favors the spread of the disease. Infection by coccidial protozoa is, for the most part, species specific. Numerous species, however, can infect a single host. For example, there are seven species of coccidial protozoa which infect chickens, six of which are considered to be moderately to severely pathogenic.

The life cycle of the coccidial parasite is complex. For example, protozoa of the genera *Eimeria, Isospora, Cystoisospora*, or *Cryptosporidium* typically only require a single host to complete their life cycle, although *Cystoisospora* may utilize an intermediate host. Under natural conditions, the life cycle begins with the ingestion of sporulated oocysts from the environment. Oocysts are generally ovoid to ellipsoid in shape, range from 10-48 µm in length by 10-30 µm in width, and may contain specialized structures, such as polar caps, micropyles, residual and crystalline bodies. When sporulated oocysts are ingested by a susceptible animal, the wall of the sporulated oocyst is broken in order to release the sporocysts inside. In poultry, the release of the sporocyst is the result of mechanical disruption of the sporulated oocyst in the gizzard. Within the sporocysts, are the sporozoites which are the infective stage of the organism. In poultry, the breakdown of the sporocyst coat and release of the sporozoites is accomplished biochemically through the action of chymotrypsin and bile salts in the small intestine. Once released, the sporozoites invade the intestinal mucosa or epithelial cells in other locations. The site of infection is characteristic of the species involved. For example, in the genus *Eimeria, E. tenella* is localized in the ceca; *E. necatrix* is found in the anterior and middle portions of the small intestine; *E. acervulina* and *E. praecox* occur in the upper half of the small intestine; *E. brunetti* occurs in the lower small intestine, rectum, ceca, and cloaca; *E. mitis* is found in the lower small intestine, while *E. maxima* can be found in any of these physiological locations.

Once inside the host animals' cells, sporozoites develop into multinucleate meronts, also called schizonts. Each nucleus of the meront develops into an infective body called a merozoite which enters new cells and repeats the process. After a variable number of asexual generations, merozoites develop into either microgametocytes or macrogametes. Microgametocytes develop into many microgametes which, in turn, fertilize the macrogametes. A resistant coat then forms around the resulting zygotes. The encysted zygotes are called oocysts and are shed unsporulated in the faeces. Infected birds may shed oocysts in the faeces for days or weeks. Under proper conditions of temperature and moisture, the oocysts become infective through the process of sporulation. Susceptible birds then ingest the sporulated oocysts through normal pecking activities or ground/litter foraging and the cycle repeats itself. Ingestion of viable, sporulated oocysts is the only natural means of infection. Infection with coccidial protozoa results in immunity so that the incidence of the disease decreases over time as members of the flock become immune. This self-limiting nature of coccidial infections is widely known in chickens and other poultry. The immunity conferred, however, is species specific such that introduction of another species of coccidial protozoa will result in a new disease outbreak.

The oocyst wall of coccidial protozoa provides a highly effective barrier for oocyst survival. Oocysts may survive for many weeks outside the host. In the laboratory, intact oocysts are resistant to extremes in pH, detergents, proteolytic, glycolytic, and lipolytic enzymes, mechanical disruption, and chemicals such as sodium hypochlorite and dichromate.

Two methods are currently used to control coccidiosis in poultry. The first involves control by chemotherapy. Numerous drugs are available for the control of coccidiosis in poultry. Because of the number of species which cause the disease, very few drugs are efficacious against all species, although a single drug may be efficacious against several species. In modern broiler chicken production, for example, administration of drugs to control coccidiosis is routine. The expense for preventative medication against coccidiosis represents a significant cost of production.

Vaccination of birds against coccidiosis is an alternative to chemotherapy. An advantage of vaccination is that it can greatly reduce or eliminate the need to administer anticoccidial drugs, thus reducing drug costs to poultry producers, preventing the development of drug-resistant strains, and lessening consumer concerns about drug residues. Numerous methods have been developed to immunize poultry against coccidial protozoa. The successful methods have all been based on the administration of live protozoa, either fully virulent strains or attenuated strains. The most common route of administration is oral, although other routes have been used. Typically, chickens are vaccinated by oral administration either directly into the mouth or via the feed or water of viable sporulated oocysts.

Regardless of the route of administration, procedures for the production of coccidiosis vaccines are quite similar. Briefly, coccidial protozoa are produced by infecting host animals with a single species of coccidial protozoa. These "seed stocks" are often clonal in nature, that is, derived from a single organism in order to insure the presence of only the species of interest. Seed stocks may be wild type, that is, isolated from the field, or they may be precocious or attenuated strains. The protozoa are then allowed to undergo replication in the host, after which, protozoa are collected from the animals, usually from the excreta. The use of attenuated strains typically results in fewer shed oocysts from the host animal. In a first step of the purification process, if needed, a coarse fraction comprising macroscopic particulate matter is separated from diluted excreta. The protozoa are then separated from the diluted excreta by well known techniques such as salt floatation and centrifugation (to ensure that no particulate matter having a density that is more than 10% different from the density of the oocysts is purified with the oocysts). At the time of collection, the protozoa are at the non-infective oocyst stage of the life cycle. In order to become infective, and therefore useful for vaccines, the oocysts must be induced to undergo sporulation. In members of the genus *Eimeria*, sporulation typically involves the incubating the oocysts in a 1% to 4% aqueous solution of potassium dichromate at 19° C. to 37° C., preferably around 28° C. (i.e. from 27.5 to 28.5° C.) with constant aeration. Sporulation is usually complete within 12 to 48 hours depending on the temperature used, and typical yield are 40-60% (meaning that 40-60% of the originally present viable oocysts are sporulated). Monitoring of the sporulation process is accomplished by microscopic examination of the protozoa. Storage compositions found in the prior art typically include an aqueous solution of potassium dichromate. The sporulated oocysts are usually stored in 1 to 4% aqueous solution of potassium dichromate to prevent bacterial growth, however, other storage media have been used.

Current vaccines available for the prevention of coccidiosis typically contain a 2.5% weight to volume solution and contain approximately 1,600 oocyts per dose (400 sporulated oocysts representing four different species). The current commercially available vaccines contain from about 0.016 μg of potassium dichromate per oocyst to about 0.16 μg of potassium dichromate per oocyst. Although widely used for sporulation and storage, potassium dichromate has several properties which make its elimination from biologicals highly desirable. Potassium dichromate is a strong oxidizer and has been reported to affect the respiratory system, liver, kidneys, eyes, skin and blood. It is a known carcinogen and upon disposal is regarded as a hazardous waste. Because of its high toxicity, compounds containing potassium dichromate are particularly unsuitable for parenteral administration. Thus, it would be highly advantageous to eliminate potassium dichromate from the production and storage of materials to be administered to animals, especially food animals.

OBJECT OF THE INVENTION

It is an object of the invention to devise a method to sporulate coccidial oocysts, which method at least mitigates disadvantages of known prior art methods, in particular, to provide a method that does not depend on the presence of potassium dichromate while being able to achieve a high yield in sporulation, preferably above 60%, more preferably even above 80%. It is also an object of the invention to provide a vaccine containing sporulated oocysts and no potassium dichromate.

SUMMARY OF THE INVENTION

In order to meet the object of the invention, a method according to the GENERAL FIELD
OF THE INVENTION section has been devised, wherein the method further comprises providing the purified oocysts as a layer on a supporting surface, maintaining the layer at least intermittently in an oxygen containing gaseous environment having a relative humidity of at least 15% and maintaining the temperature of the oocysts between 19° C. and 37° C.

In prior art methods, sporulation involves incubating the oocysts in an aqueous solution of potassium dichromate with constant aeration. This provides for the necessary water, oxygen and adequate temperature needed for sporulation to take effect. Applicant however found that it is better to keep the oocysts, at least intermittently, in a gaseous environment rather than in the aqueous environment as teached in the prior art. It was found that this way no potassium dichromate is needed, provided that the oocysts are kept sufficiently moist (above 15%, as known from Waldenstedt et al, 2001 Poultry science 80:1412-1415) and the temperature is kept at an adequate level. Also, the yield of sporulation may be significantly increased to levels up to 80-100%. The reason for this is not completely clear but may be partly related to the fact that in an aqueous environment in a flask, even if aerated continuously, there is still a significant amount of "dead" space where there is no sufficient aeration. Also, continuously aerating leads to a continuous significant tumbling of the oocysts in the flask which gives rise to continuous mechanical load on the oocysts. This may explain that part of the viable oocysts gets lost. Also, it may be that in an aerated aqueous solution, the level of available oxygen is still too low to favour sporulation of a large part of the oocysts.

In any case, applicant found that by subjecting the oocysts to a gaseous environment when being present in the form of a layer on a supporting surface, very good sporulation can be achieved, without needing any potassium dichromate, provided that the oocysts are sufficiently moist and the temperature of the oocysts is maintained between 19° C. and 37° C. The temperature may have any value between 19 and 37° C., i.e. 20, 21, 22, 23, 24, 25, 26, 27, 28, 29, 30, 31, 32, 33, 34, 35 or 36° C. or any value in between these temperatures. With regard to the humidity, although a level of 15% relative humidity may be sufficient to support sporulation, a higher level is preferred since that way, the risk of the oocysts in the layer getting too dry is decreased. Therefore the level of relative humidity of the gaseous environment may have any of the following values (% relative humidity) up to and including 100%: 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99. At a relative humidity of 100% a thin water film will form on the layer of oocysts. Applicant found that such a thin layer has no detrimental effect on the sporulation process as long as gas transport (for example of oxygen consumed by the oocysts and resulting gases produced by the oocysts) by diffusion can keep up with use and/or production of gas by oocysts. Such a thin layer of water thus still means that effectively the layer of oocysts can be considered to be present in a gaseous environment in the sense of the present invention.

According to the invention, sporulated oocysts can be obtained at adequate yield, wherein the sporulated oocysts do not contain residues of potassium dichromate and thus, a vaccine based on such oocysts also does not contain this salt.

The invention also pertains to a composition containing sporulated coccidial oocysts obtainable with a double sieving method as described here above, the coccidial oocysts having dimensions between Dmin and Dmax, wherein the composition contains particles having dimensions between Dmin and Dmax which particles have a density different from the density of the oocysts.

DEFINITIONS

A oocysts composition purified from faeces means that at least 90%, in particular 91, 92, 93, 94, 95% or more of the non-oocysts material is removed from the faeces wherein the oocysts were excreted.

A macroscopic object is an object that can be seen with the unaided human eye. Typically, this means that the object has a dimension of at least about 0.1 mm.

A particle is a localized microscopic or macroscopic object to which can be ascribed physical properties such as volume and mass. Typical particles present in animal faeces are sand grains, silt particles, clay particles, remains of plants (digested and undigested), oil droplets, bacteria, viruses, grit, pebbles etc.

A mesh opening of a sieve deck is equal to the diameter of an imaginary circle that fits the actual opening in the deck. A mesh opening is inherently "around" a predetermined size since a surface with multiple mesh openings cannot be made with exactly the same dimension for all openings, and also is subject to variation under mechanical load (mass on sieve deck, vibrating etc). A mesh opening is typically an effective average around a predetermined size. In this respect "around value X" for a mesh size means than in practice the actual size of an opening may vary between 0.9 and 1.1 times X, in particular between 0.95 and 1.05 times X, and preferably between 0.98 and 1.02 times X.

For an object to extend in a direction means that the object at least partly extends in that direction, preferably substantially extends in that direction, i.e. the object extends in that direction more than in any other direction.

EMBODIMENTS

In a first embodiment of the method according to the invention the thickness of the layer is below 10 mm. Applicant found that when the thickness of the layer is at most equal to the regular maximum cross sectional dimension of a regular chicken dropping, which is about 10 mm, a substantial part of the oocysts, if not almost all, can sporulate. It was applicants' recognition that the dimension of a regular chicken dropping is such that even oocysts at the bottom of the dropping may sporulate in the gaseous environment they reside in (i.e. a regular chicken housing). In other words, a layer of around 10 mm thick may allow a diffusion of oxygen such that a substantial part of the oocysts may sporulate. The thickness may even be below 9 mm, 8 mm, 7 mm, 6 mm, 5 mm, 4 mm, 3 mm, 2 mm or 1 mm. Typically the thickness of the layer is between 0.5 and 5 mm.

In a next embodiment the supporting surface is a perforated deck that is able to let water pass. In this embodiment the layer of oocysts can be kept wet by providing water to the layer (for example in the form of a mist, shower, spray, stream etc.) but still, since the water can pass the layer through the perforated deck, the layer can in essence remain in the gaseous environment according to the invention. In a further embodiment the supporting surface has mesh openings around a minimum dimension (Dmin) of the oocysts. It was found that if the mesh openings are around Dmin, any oocysts having a smallest dimension of Dmin are obstructed in passing the perforated deck, while bacteria, viruses, protein flocks and other particles having a typical dimension smaller than Dmin may pass the deck together with the water. This provides for an extra cleaning step of the oocysts while sporulating. In the prior art methods, any bacteria and viruses remained in the flask with the oocysts. In principle however, a critical situation could be arrived at if the aqueous fraction to be filtered would have too many non-oocyst particles having a dimension just below Dmin, since such particles would typically also be somewhat obstructed and might thus remain as a contamination in the oocysts layer. However, such critical particles appear to be not (reasonably noticeable) present in animal faeces, and thus, using a mesh size around Dmin appears to be perfectly suitable to keep the oocysts on the supporting surface while smaller contaminant particles will pass this perforated surface. In yet a further embodiment the supporting surface has mesh openings around 10 μm. Mesh openings of this size appear to be ideally suitable to support a layer of oocysts of any size, even if for example the oocysts to be purified range are in size between 20-35 μm in length and 20-30 μm in width. The size of the openings, i.e. 10 μm, appears to be suitable to keep oocysts of various sizes on the supporting surface and still, any "fines" (typically bacteria, viruses or other micro organisms) below 10 μm can be washed out by using water to rinse the layer.

In an embodiment the supporting surface is in the form of an endless perforated deck. In this embodiment the layer could be provided on the inside or outside of the deck. This allows a relatively big surface to be available for supporting the layer while the footprint is still relatively low. In a further embodiment the perforated deck is drum shaped. This way, an even distribution of the oocysts in the layer can be provided easily in order to assure comparable circumstances throughout the layer. In yet a further embodiment the endless deck is placed partly in a volume of water and partly in the gaseous environment, mounted with its longitudinal axis extending in parallel with a surface of this volume of water and wherein the deck is rotated for maintaining the layer at least intermittently in the oxygen containing gaseous environment. This way, the oocysts in the layer can be kept at a high moist level, up to 100%, even if the gaseous environment is relatively dry, simply since the oocysts intermittently travel through the volume of water. This appears to be a very simple but adequate way of providing two main requirements for the present invention: keeping the oocysts at least intermittently in a gaseous environment and prevent them from drying. By rotating the drum the oocysts in the layer rotate partly in the upper part of the drum which is in a gaseous environment, and partly in the lower part of the drum which is in an aqueous environment. The positioning of the endless deck in the volume of water is typically such that at most half of the inner space of the endless deck is submerged in the water, or even only 5-30%, or 5-20%. Preferably the drum is rotated at an rpm such that the layer travels at a speed of 10 meters/minute (m/min) to 40 m/min, being the circumferential speed of the drum. Below this speed it may be that the oocysts in the layer, at low relative humidity of the gaseous environment, get too dry, while above 40 m/min the oocysts might face too much mechanical forces and get damaged. For a drum having a diameter of 80 cm, the corresponding rpm level is 5-20 rpm. The corresponding circumferential speed appears to be ideally suitable, in particulate when combined with a submerge level of 5-30% (as indicated here above) to provide for an adequate duration of the layer in the gaseous environment while at the same time preventing that the layer becomes too dry throughout the range of allowed relative humidity for the gaseous environment.

In an embodiment the layer of oocysts is provided on the internal surface of the endless deck. This embodiment makes it easier to keep the oocysts on the supporting surface. Although due to the rotation of the layer through the volume of water, at least a part of the oocysts in the layer may leave the layer and for a while stay in the volume of water, ultimately they are picked up again by the rotating deck.

In another embodiment the volume of water is kept at a temperature between 19° C. and 37° C. In this embodiment the water is used to keep the temperature of the oocysts at an adequate level to support sporulation. Preferably the volume of water is kept at a temperature of about 28° C. which is the ideal temperature to support sporulation.

In still another embodiment, after sporulation of the oocysts, a further aquous medium containing an antiinfective is provided to the layer, whereafter the layer is washed to remove the anti-infective. In this embodiment remaining contaminants can be removed while the layer is still intact. In the prior art washing sporulated oocysts with an antiinfective has also been described, but for this the oocysts need to be taken out of their sporulation flask and treated in a separate washing process.

In yet another embodiment wherein the supporting surface is a sieve deck having an effective mesh opening around the minimum dimension of the oocysts (Dmin), the thin layer is provided by collecting faeces of animals containing the coccidial oocysts, diluting the faeces in an aqueous medium, and separating a coarse fraction comprising macroscopic particulate matter from the diluted faeces, and collecting an aqueous fraction containing the oocysts, sieving the aqueous fraction over a first sieve deck other than the said supporting surface, the first sieve deck having mesh openings to let the oocysts pass in order to obtain an aqueous filtrate comprising the oocysts and a residue on the first sieve deck comprising particles larger than the oocysts, and then sieving the aqueous filtrate over the said supporting surface. Applicant found that by applying a simple two-step sieving process, oocysts can be purified to an adequate level from the aqueous fraction of the faeces. In the first sieving step the particles coarser than the oocysts (typically sand grains, grit and remains of plants) can be removed, while in the second sieving step the particles smaller than the oocysts (typically bacteria, viruses, digested remains of plants, protein flocks, oil droplets etc.) can be removed. Sieving can be applied (semi-) continuously and the amount of water present in the aqueous fraction in relation to the amount of oocysts is not bound to any economical maximum: the water ultimately passes the second sieve deck while the purified oocysts remain as a thin layer residue on this deck. This way, water can be effectively used to obtain a good sieving and cleaning action.

In the art, sieving has never been used or even suggested as a method to purify coccidial oocysts from faeces. Although sieving has been used to remove a coarse fraction from the faeces, it has never been used to obtain purified oocysts. Without being bound to theory, there appear to be several reasons for this. Firstly, the common methods used for purifying oocysts are all based on using the particular density of the oocysts, since it is understood that in the faeces, no other major fractions are present that have the same density (i.e. having a density within a density range being at most 10%, or even at most 9, 8, 7, 6, 5, 4, 3, 2 or even as little as 1% different from the density of the oocysts) as the oocysts. Therefore, such methods can lead to an adequately pure oocysts composition. With sieving, one cannot discriminate between particles having different densities, but only between particles having different sizes. This inherently leads to the fact that with sieving, other particles in the same size range as the oocysts, but having another density are incorporated as an additional contamination in the oocysts fraction. Therefore it is commonly expected that with sieving the oocysts cannot be purified to an adequate level. Also, oocysts are not perfectly spherical but generally ovoid to ellipsoid in shape. Sieving non-spherical particles has the inherent problem that the sieving action depends on the orientation particles take with regard to the sieve deck. Since this orientation cannot be controlled, sieving is often not regarded a viable option for precisely fractioning non spherical particles. Lastly, sieving often leads to a high mechanical load on the particles being sieved, in particular when the mesh size is in the same range of the particle size. For biological matter, such a high mechanical load is often detrimental for their viability (cf. the commonly used French Press method for killing bacteria). To applicant's surprise, none of all this prevents sieving from being a good method to purify coccidial oocysts from faeces and obtain a purity that is adequate for using the oocysts in an effective vaccine.

The invention will now be further explained, based on the following figures and examples.

EXAMPLES

FIG. 1 diagrammatically shows a system for collecting oocysts for sporulation.

Figure 2:
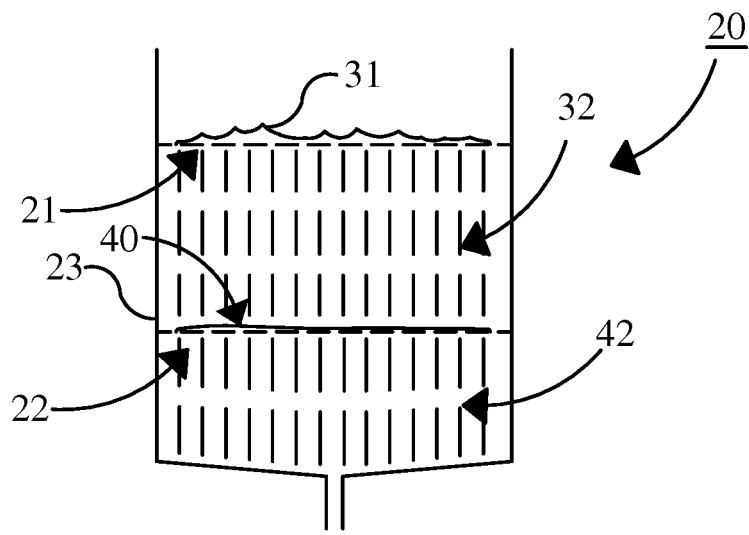

FIG. 2 schematically shows an embodiment of a system according to the invention.

Figure 3:
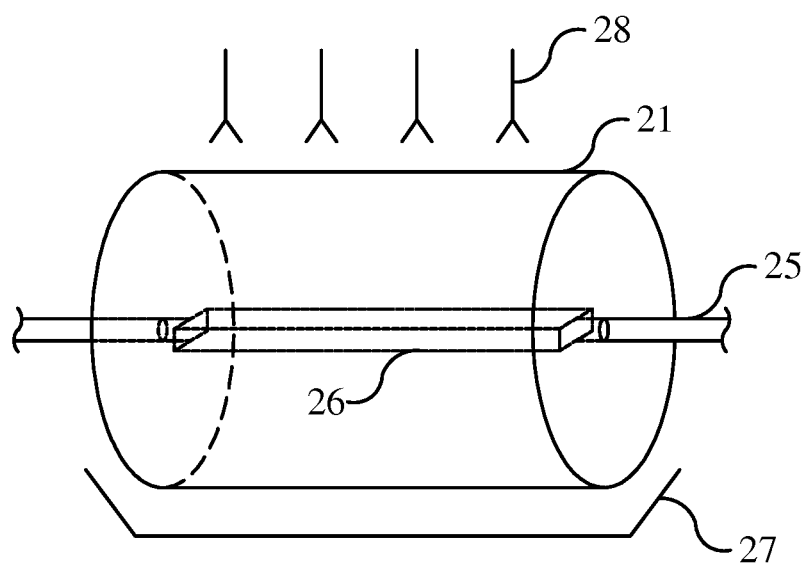

FIG. 3 schematically shows an embodiment of a sieve deck for use in a method or system according to the invention.

Figure 4:
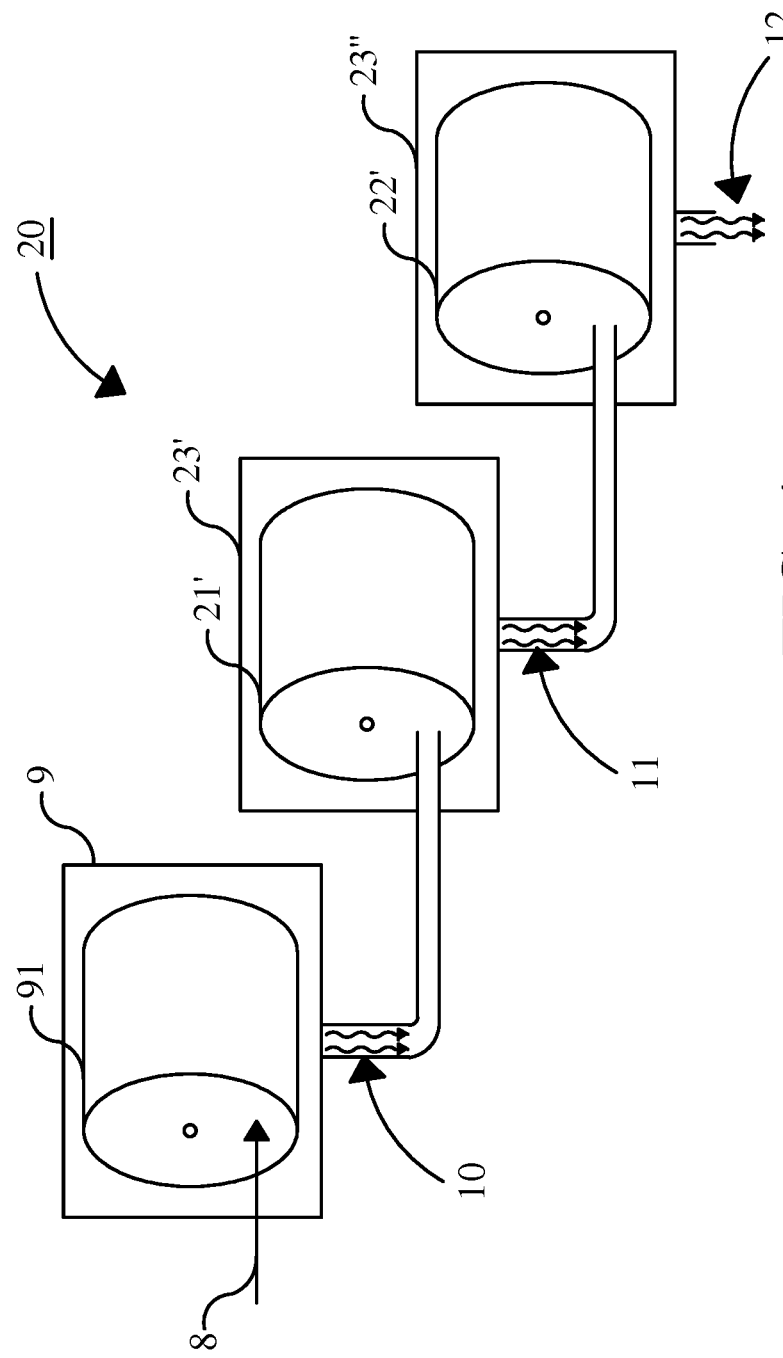

FIG. 4 schematically shows another embodiment of a system according to the invention.

Figure 5:
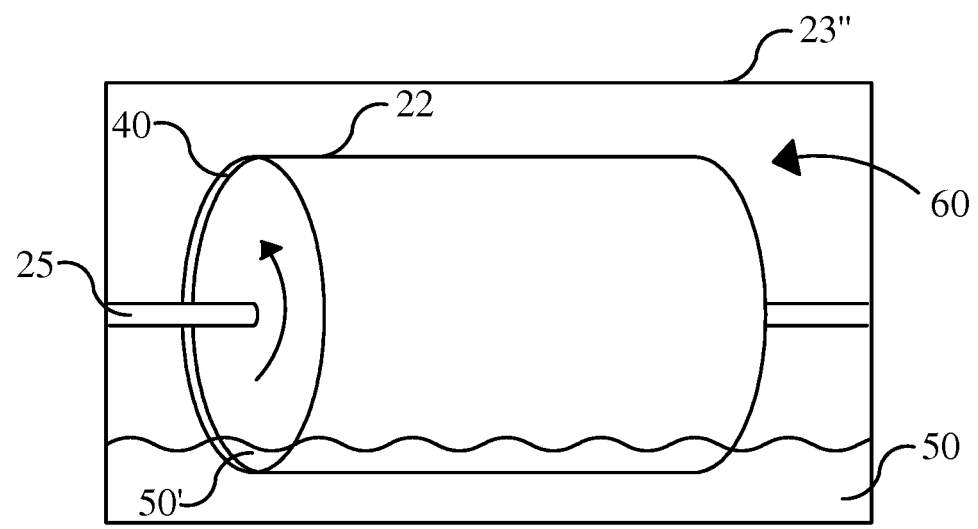

FIG. 5 schematically shows a sieve deck for use as a support to let purified oocysts sporulate.

Example 1 describes process data regarding a method according to the invention.

FIG. 1

FIG. 1 diagrammatically shows a system for collecting animal faeces containing coccidial oocysts from host animals, and separating a coarse fraction comprising macroscopic particulate matter from the faeces and collecting a fraction containing the oocysts for further purification. In general, a number of different methods of preparing oocysts for further purification are known in the art. Any one or combination of such methods may be used prior to further purification. A preferred method is set out below.

To begin, once host animals (typically chickens) begin shedding the organism, the oocysts can be collected. Most commonly, the chickens are kept in cages (1), and are fed solid food (2) and water (3). Faeces 5 are collected from the cages, and a waste stream containing other material (feathers, straw etc) is discarded. Once collected, the faeces are brought over to a slurry tank 6 and mixed with added water (7). The resulting diluted fecal material is provided to a sieve 9 for removal of the coarse material in the faeces such as stones, remains of shavings, grid, remains of animal feed etc. For this, the sieve comprises two consecutive plate sieves, the upstream sieve having mesh openings of 2 mm, and the downstream sieve having mesh openings of 125 µm. The resulting residues (11) are discarded, and the filtrate is collected as an aqueous fraction 10 containing the oocysts.

FIG. 2

FIG. 2 schematically shows an embodiment of a system 20 according to the invention. In this embodiment the system comprises a longitudinal, tube-like housing 23 having two internal sieve decks, viz. an upstream sieve deck 21 and a downstream sieve deck 22. In this embodiment the sieve decks are made of woven stainless steel wires, according to a plain weaving pattern. The aqueous fraction 10 (see FIG. 1) is provided to the top of sieve deck 21 in order to sieve this fraction. This deck has mesh openings such that the oocysts pass to obtain an aqueous filtrate 32 comprising the oocysts, and a first residue 31 comprising particles larger than the oocysts. The aqueous filtrate 32 is provided to the top of second sieve deck 22, which sieve deck has mesh openings to obstruct passing of the oocysts through this sieve deck. This way a second residue 40 comprising the purified oocysts and a waist filtrate 42 comprising particles smaller than the oocysts is obtained.

The size of the mesh openings should be chosen to effective collect oocysts of the desired shape. For example, to collect oocysts of a size range between 15 and 25 μm, the first sieve deck may have mesh openings of 25 μm, and the second sieve deck may have mesh openings of about 14 μm. In this case, since the mesh openings correspond almost exactly with the size of oocysts, a lot of additional water may be needed (provided as a separate feed to the top of sieve deck 21) to actually have the oocysts pass the first sieve deck. In another set-up, for example to collect oocysts of a size range between 20 and 30 μm, the first sieve deck may have mesh openings of 40 μm, and the second sieve deck may have mesh openings of about 15 μm. In yet another set-up, for example to collect oocysts of a size range between 10 and 40 μm, the first sieve deck may have mesh openings of 42 μm, and the second sieve deck may have mesh openings of about 10 μm. In still another embodiment, for example to collect oocysts of a size range between 12 and 48 μm, the first sieve deck may have mesh openings of 50 μm, and the second sieve deck may have mesh openings of about 10 μm.

FIG. 3

FIG. 3 schematically shows an embodiment of a sieve deck 21 (mesh openings 50 μm) for use in a method or system according to the invention. In this embodiment, the sieve deck is an endless deck in the form of a drum. The drum is rotatably supported on axis 25 and is internally provided with a stationary container 26. In use, the aqueous fraction is loaded on the inside of this drum, below the container 26, and the drum is rotated while sieving the aqueous fraction. Also, during this sieving action additional aqueous medium having a temperature of about 28° C. is added to the inside of the drum 21. The aqueous filtrate is collected in container 27. Above the drum is situated a row of spray heads 28. These heads can be used to add water to the drum, either to serve as a lubricant whilst sieving, or, after the sieving has ended, to release the residue from the drum and collect it in the container 26. This container can be removed by sliding it over axis 25.

FIG. 4

FIG. 4 schematically shows another embodiment of a system 20 according to the invention, in which embodiment a semi continuous process for applying the method according to the invention can be run. This system comprises a rotating sieve 91 (having mesh openings of 150 μm), which is surrounded by housing 9. This sieve and housing correspond to item 9 in FIG. 1. To this sieve 91 an aqueous fraction 8, comprising diluted chicken faeces (see FIG. 1, albeit that this fraction is optionally pre-sieved over a 2 mm sieve), is fed for separating the coarse fraction comprising macroscopic particulate matter from the diluted faeces. The aqueous fraction 10 containing the oocysts is collected and fed to drum-shaped rotated sieve 21' (see also FIG. 3) as present in housing 23'. As described in conjunction with FIG. 3, this sieve deck has mesh openings of 50 μm and separates the aqueous fraction in an aqueous filtrate 11 comprising the oocysts and a first residue (not shown), comprising particles larger than the oocysts. This residue can be removed as described here above. The aqueous filtrate 11 is fed to rotating sieve 22', which sieve is housed in housing 23". This sieve 22' has mesh openings of 10 μm to obstruct passing of the oocysts through this sieve deck, such that a residue comprising the purified oocysts is build up on the internal side of this drum-shaped sieve deck 22'. The waist filtrate 12 comprises particles smaller than the oocysts, such as any bacteria.

FIG. 5

FIG. 5 schematically shows a sieve deck for use as a support to let purified oocysts sporulate. In this embodiment, the residue 40 is build up as a 2.5-3.5 mm layer on the inside of sieve deck 22 (having mesh openings of 10 μm). The drum-shaped sieve deck 22 is placed partly in a volume of water (50; kept at a temperature of 28° C.) and partly in the gaseous environment 60, such that about 20% of the total circumference of the drum is below the level of the volume of water. The drum is mounted with its longitudinal axis 25 extending in parallel with the surface of this volume of water. During sporulating the drum is rotated for maintaining the layer 40 intermittently in the oxygen containing gaseous environment 60. The drum is revolved at 10-12 rpm through the water 50'. The relative humidity of the gaseous environment in the drum is 100%. It was found that this way the oocysts can sporulate (almost all) within 48 hours.

Example 1

Example 1 describes process data regarding a method according to the invention using the system of FIG. 4. In this system small drum shaped decks are used having a length of 40 cm and a drum diameter of 80 cm (drums having a length of up to 2.80 meters and a diameter of up to 2.0 meters can be advantageously used in the set-up of FIG. 4). The decks have meshes of stainless steel wires woven according to a plain weave, with mesh openings as described in conjunction with FIG. 4. The drums rotate at 10-12 revelations per minute.

The faeces of 60 white leghorn chickens (infected with *Eimeria*) aged 26-31 days was collected (approximately 25 grams of faeces per chicken per day), mixed with 200 liters of water, and the coarse fraction was separated using a 2 mm sieve. Approximately 50 liters of this mixture (containing about 2.25 kg of faeces) was loaded into the system, wherein during sieving about 5-10 liters of water per minute was added to sieve decks 21 and 22. This resulted in about 120 grams of purified oocysts (a composition containing an estimated amount of about 85 grams of non oocysts faecal particles, typically fine sand grains, silt and clay particles, and about 35 grams of oocysts) on sieve deck 22 after 35 minutes of sieving, at a calculated yield of approximately 81% for *Eimeria acervulina* and approximately 100% for *Eimeria maxima*. Using the traditional method of flotation and centrifugation, this takes about 6 hours, with typical yields of about 50-60% for both species.

Optionally, depending on the amount of contamination still present an additional washing step may be performed by mixing the residue in a 6% hypochlorite (anti-infective) solution and load it into drum 22. Water is continuously added at about 5-10 liters per minute to remove the hypochlorite, and after 15 minutes the residue is ready for further processing.

After sporulating as described in conjunction with FIG. 5, typical sporulating rates are 85% for *Eimeria acervulina* and 90% for *Eimeria maxima* (cf typical values of 40% to a maximum of 80% for the traditional process using potassium dichromate). These sporulated oocysts can serve as antigen in a coccidiosis vaccine as known in the prior art.

The invention claimed is:

1. A method to sporulate coccidial oocysts purified from animal faeces, the method comprising providing the purified oocysts as a layer on a supporting surface, maintaining the layer at least intermittently in an oxygen containing gaseous environment having a relative humidity of at least 15% and maintaining the temperature of the oocysts between 19° C. and 37° C.

2. The method of claim 1, wherein the thickness of the layer is below 10 mm.

3. The method of claim 1, wherein the supporting surface is a perforated deck that is able to let water pass, but does not let the oocysts pass.

4. The method of claim 3, wherein the supporting surface has mesh openings around a minimum dimension of the oocysts.

5. The method of claim 3, wherein the supporting surface has mesh openings around 10 μm.

6. The method of claim 1, wherein the supporting surface is in the form of a perforated deck that is drum shaped, and wherein the layer of oocysts is provided on the internal surface of the drum-shaped deck.

7. The method of claim 6, wherein the drum-shaped deck is placed partly in a volume of water and partly in the gaseous environment, mounted with its longitudinal axis extending in parallel with a surface of this volume of water, wherein the deck is rotated for maintaining the layer at least intermittently in the oxygen containing gaseous environment, and wherein the drum-shaped deck is rotated around its longitudinal axis.

8. The method of claim 7, wherein the drum-shaped deck is rotated at a circumferential speed of 5-20 rpms.

9. The method of claim 7, wherein the volume of water is kept at a temperature between 19° C. and 37° C.

10. The method of claim 7, wherein the volume of water is kept at a temperature of about 28° C.

11. The method of claim 1, wherein after sporulation of the oocysts, a further aqueous medium containing an anti-infective is provided to the layer to remove contamination by a sieving step, whereafter the layer is washed to remove the anti-infective.

12. The method of claim 1, wherein the supporting surface is a sieve deck having an effective mesh opening around the minimum dimension of the oocysts, wherein a thin layer is provided by collecting faeces of animals containing the coccidial oocysts, diluting the faeces in an aqueous medium wherein separating a coarse fraction comprising macroscopic particulate matter from the diluted faeces is optional, and collecting an aqueous fraction containing the oocysts, sieving the aqueous fraction over a first sieve deck other than the said supporting surface, the first sieve deck having mesh openings to let the oocysts pass in order to obtain an aqueous filtrate comprising the oocysts and a residue on the first sieve deck comprising particles larger than the oocysts, and then sieving the aqueous filtrate over the said supporting surface.

* * * * *